US00PP27414P2

(12) United States Plant Patent
Probst

(10) Patent No.: US PP27,414 P2
(45) Date of Patent: Nov. 22, 2016

(54) ***COREOPSIS* PLANT NAMED 'BERRY CHIFFON'**

(50) Latin Name: ***Coreopsis* hybrid**
Varietal Denomination: Berry Chiffon

(71) Applicant: Darrell R. Probst, Hubbardston, MA (US)

(72) Inventor: Darrell R. Probst, Hubbardston, MA (US)

( * ) Notice: Subject to any disclaimer, the term of this patent is extended or adjusted under 35 U.S.C. 154(b) by 0 days.

(21) Appl. No.: 14/756,516

(22) Filed: Sep. 14, 2015

(51) Int. Cl.
*A01H 5/02* (2006.01)

(52) U.S. Cl.
USPC ..... Plt./417

(58) Field of Classification Search
USPC ..... Plt./417
See application file for complete search history.

*Primary Examiner* — Annette Para
(74) *Attorney, Agent, or Firm* — Penny J. Aguirre

(57) ABSTRACT

A new cultivar of hybrid *Coreopsis* named 'Berry Chiffon' characterized by its sturdy, upright plant habit, its medium sized inflorescences with ray florets that are creamy white in color with a large plum colored eye zone, its nearly sterile flowers that exhibit a floriferous and long bloom season that does not require deadheading, its cold hardiness to at least U.S.D.A. Zone 5, and its resistance to powdery mildew and leaf spot.

2 Drawing Sheets

Botanical classification: *Coreopsis* hybrid.
Variety denomination: 'Berry Chiffon'.

BACKGROUND OF THE INVENTION

The present invention relates to a new and distinct cultivar of a plant botanically of hybrid origin and known as *Coreopsis*. The new cultivar will be referred to hereafter by its cultivar name 'Berry Chiffon'. 'Berry Chiffon' is an herbaceous perennial grown for landscape and container use.

The new invention arose from an ongoing controlled breeding program in Hubbardston, Mass. The objective of the breeding program is to develop hybrid cultivars of *Coreopsis* with unique and superior garden attributes. In particular, to develop cultivars that are long-lived, sturdy, exhibit a true perennial habit and are cold hardy to at least U.S.D.A. Zone 5 in a wide range of flower colors and plant forms.

The Inventor made a controlled cross in August of 2011 in his test garden in Hubbardston, Mass. between an unnamed proprietary plant from the Inventor's breeding program, reference no. J 06-1, as the female parent and an unnamed proprietary plant of *Coreopsis* as the male parent. 'Berry Chiffon' was selected in September 2012 as a single unique plant amongst the resulting seedlings.

Asexual propagation of the new cultivar was first accomplished by stem cuttings in Kensington, Conn. in September 2012 under the direction of the Inventor. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Berry Chiffon' as unique cultivar of *Coreopsis*.

1. 'Berry Chiffon' exhibits a sturdy and branched plant habit.
2. 'Berry Chiffon' exhibits medium sized inflorescences with ray florets that are creamy white in color with a large plum colored eye zone.
3. 'Berry Chiffon' exhibits nearly sterile flowers that exhibit a floriferous and long bloom season that does not require deadheading with bloom commencing in early July and lasting until frost in Kensington, Conn.
4. 'Berry Chiffon' exhibits cold hardiness to at least U.S.D.A. Zone 5.
5. 'Berry Chiffon' exhibits resistance to powdery mildew and leaf spot.

The female parent of 'Berry Chiffon', J 06-1, differs in having inflorescences with ray florets that are bright yellow in color, in having a taller plant height, and in having a floppy plant habit. 'Berry Chiffon' can be compared to the *Coreopsis* cultivars 'Ruby Frost' (U.S. Plant Pat. No. 21,758) and 'Show Stopper' (U.S. Plant Pat. No. 22,671). 'Ruby Frost' is similar to 'Berry Chiffon' in having white inflorescences with a large red-purple eye zone and in having thread leaf type foliage. 'Ruby Frost' differs from 'Berry Chiffon' in being less cold hardy and in being prone to powdery mildew when grown under the same conditions in Hubbardston, Mass. 'Show Stopper' is similar to 'Berry Chiffon' in having flowers that are primarily purple in color and in having thread leaf type foliage. 'Show Stopper' differs from 'Berry Chiffon' in having inflorescences with ray florets that are pinkish-purple in color, in being relatively fertile, in being prone to powdery mildew when grown under the same conditions in Hubbardston, Mass., and in being less cold hardy.

BRIEF DESCRIPTION OF THE DRAWINGS

The accompanying colored photographs illustrate the overall appearance and distinct characteristics of the new *Coreopsis*. The photographs were taken of a three month-old plant of 'Berry Chiffon' as grown outdoors in one-gallon containers from a 128-cell plug in Kensington, Conn.

The photograph in FIG. 1 provides a side view of a plant of 'Berry Chiffon'.

Figure 1:
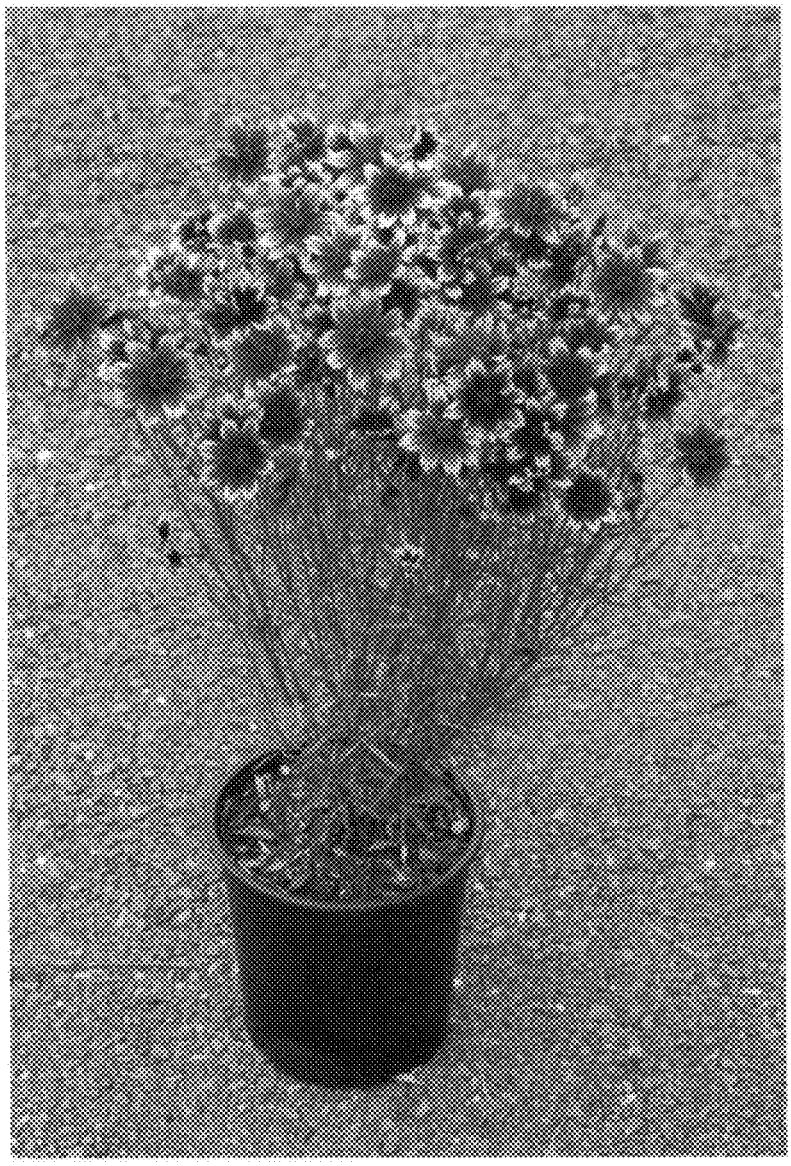
Figure 2:
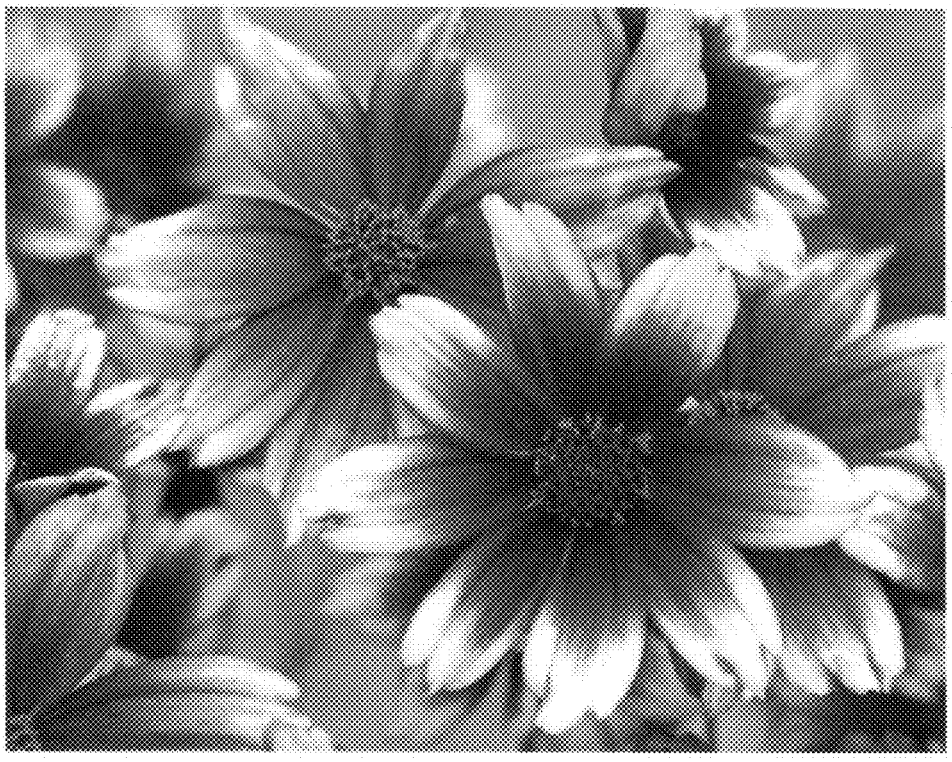

The photograph in FIG. 2 provides a close-up view of the inflorescence of 'Berry Chiffon'.

The colors in the photographs may differ slightly from the color values cited in the detailed botanical description, which accurately describe the colors of the new *Coreopsis*.

DETAILED BOTANICAL DESCRIPTION

The following is a detailed description of three month-old plants of the new cultivar as grown outdoors in one-gallon containers in Kensington, Conn. from 128-cell plugs. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Blooms from early July until frost in Kensington, Conn.

*Plant type*.—Herbaceous perennial.

*Plant habit*.—Clump-forming and densely branched.

*Height and spread*.—An average of 45 cm in height and 55 cm in width in the when planted in the landscape.

*Cold hardiness*.—At least in U.S.D.A Zone 5.

*Diseases resistance*.—Has been observed to be highly resistant to powdery mildew caused by *Podosphaera macularis* and leaf spot by *Pseudomonas cichorii*.

*Root description*.—Fibrous when young, becoming fleshy with age.

*Propagation*.—Division and stem cuttings (preferred).

*Growth rate*.—Vigorous.

*Root development*.—Roots initiate in 6 to 8 days and fully develop in a 128-cell plug in about 28 days with bottom heat and rooting hormone at optimal times of the year.

Stem description:

*Shape*.—Oval, ridged.

*Stem color*.—Young; 146A, mature bark; 146A heavily suffused with 183A.

*Stem size*.—Main and secondary stems; an average of 20 cm in length and 3 mm in width, secondary, tertiary stems; 12 cm in length and 1.5 mm in width.

*Stem surface*.—Glabrous.

*Stem aspect*.—Upright.

*Branching habit*.—Well-branched, an average of 1 main branch, 6 secondary branches per main stem, and 3 tertiary branches.

*Internode length*.—An average of 4.5 cm.

Foliage description:

*Leaf division*.—Simple.

*Leaf margins*.—Entire to lobed with 3 to 5 lobes.

*Leaf size*.—Variable, up to 4 cm in length and 2 mm in width when entire, up to 6 cm in length and 3.5 cm in width when lobed.

*Leaf shape*.—Oblanceolate when entire, lobes oblanceolate.

*Leaf base*.—Truncate.

*Leaf apex*.—Acute.

*Leaf venation*.—Pinnate, inconspicuous, matches leaf color on upper and lower surface.

*Leaf attachment*.—Sessile.

*Leaf arrangement*.—Opposite.

*Leaf surface*.—Glabrous on upper and lower surface.

*Leaf color*.—Young and mature upper surface; 137A, young and mature lower surface; 137D.

Inflorescence description:

*Inflorescence type*.—Composite with a single row of ray florets surrounding disk florets in the center, forming a radiant head, inflorescences are borne on branch terminals in loose corymbs.

*Lastingness of inflorescence*.—8 to 10 days until senescence of ray flowers, longer in cool temperatures, bracts and disk flowers are persistent.

*Fragrance*.—None detected.

*Quantity of inflorescences*.—An average of 160 per main branch.

*Inflorescence size*.—Corymbs; an average of 14.5 cm in length and 4.5 in width, composite; an average of 1.6 cm in depth and up to 5 cm in diameter.

*Inflorescence buds*.—Average of 6 cm in depth and in diameter, spherical in shape with a flattened top, color; a blend of 138A, 151C, and 183B.

*Peduncle*.—Average of 6 cm in length and 1.2 mm in width, glabrous surface, 146A in color.

*Pedicle*.—Average of 7 cm in length and 1 mm in width, glabrous surface, a blend of 144A and 147A in color.

*Sepals*.—An average of 8.4 mm in length and 2 mm in width, color; 146A with margins 157B.

Involucral bracts:

*Bract number*.—8 total, 4 outer bracts and 4 inner bracts.

*Bract arrangement*.—Bracts are un-fused and overlapping surrounding the receptacle in a campanulate form and held close to lower surface of ray florets.

*Bract size*.—Outer and inner bracts; an average of 8 mm in length and 4 mm in width.

*Bract color*.—Inner bracts and outer bracts translucent; apex, 7A, base 143A, and margins 187C.

*Bract texture*.—Glabrous on outer and inner surfaces of outer and inner bracts.

*Bract apex*.—Acute to rounded on outer and inner bracts.

*Bract base*.—Truncate on inner and outer bracts.

*Bract margins*.—Entire on outer and inner bracts.

*Bract shape*.—Outer and inner bracts; ovate.

Ray florets (sterile):

*Number*.—An average of 8 arranged primarily in one row.

*Shape*.—Oval.

*Size*.—An average of 1.5 cm in length and 7 mm in width.

*Apex*.—2 notched.

*Base*.—Cuneate.

*Margins*.—Entire with apex notched.

*Aspect*.—Held outward to upward.

*Texture*.—Glabrous on upper and lower surface.

*Color*.—When opening and when fully opened inner surface; 3C, base a blend of 187B to 187C, when opening and when fully opened outer surface; 4C, base 183A.

Disk flowers (perfect):

*Shape*.—Tubular, corolla is fused, flared at apex.

*Number*.—About 80.

*Size*.—About 6 mm in length and 1 mm in width.

*Color*.—En masse; 28A, corolla tube; 154D with apices 176A in color.

*Receptacle*.—About 4 mm in diameter and 3 mm in depth, a blend of 144B to 144D in color.

Reproductive organs:

*Presence*.—Disk flowers are perfect, ray flowers are sterile.

*Gynoecium*.—1 Pistil, 5 mm in length, style is very fine, translucent and 4D in color, stigma is 176A in color, ovary is 1 mm in length, 0.5 mm in width, inferior, and 4D in color.

*Androcoecium*.—5 stamens, fused into tube surrounding style, 1 mm in length and 0.2 mm in width, about 200A in color, pollen is very low in quantity.

*Fruit/seed*.—No fruit or seed development was observed.

It is claimed:

1. A new and distinct cultivar of *Coreopsis* plant named 'Berry Chiffon' as herein illustrated and described.

* * * * *